(12) United States Patent
Fang

(10) Patent No.: US 9,914,962 B2
(45) Date of Patent: Mar. 13, 2018

(54) QUANTIFICATION OF RNA

(71) Applicant: QIAGEN GMBH, Hilden (DE)

(72) Inventor: Nan Fang, Hilden (DE)

(73) Assignee: QIAGEN GMBH (DE)

( * ) Notice: Subject to any disclaimer, the term of this patent is extended or adjusted under 35 U.S.C. 154(b) by 0 days.

(21) Appl. No.: 15/025,750

(22) PCT Filed: Sep. 12, 2014

(86) PCT No.: PCT/EP2014/069488
§ 371 (c)(1),
(2) Date: Mar. 29, 2016

(87) PCT Pub. No.: WO2015/043982
PCT Pub. Date: Apr. 2, 2015

(65) Prior Publication Data
US 2016/0244821 A1 Aug. 25, 2016

(30) Foreign Application Priority Data

Sep. 30, 2013 (EP) ..................................... 13186706

(51) Int. Cl.
*C12Q 1/68* (2006.01)

(52) U.S. Cl.
CPC ................... *C12Q 1/6851* (2013.01)

(58) Field of Classification Search
CPC .................................................. C12Q 1/6851
USPC ....................................................... 435/6.1
See application file for complete search history.

(56) References Cited

U.S. PATENT DOCUMENTS

| | | | | |
|---|---|---|---|---|
| 6,489,455 | B2 * | 12/2002 | Chenchik ............ | C12Q 1/6876 435/6.1 |
| 2004/0067492 | A1 | 4/2004 | Peng et al. | |
| 2004/0209283 | A1 | 10/2004 | Yagi et al. | |
| 2012/0219953 | A1 | 8/2012 | Fang | |

FOREIGN PATENT DOCUMENTS

| WO | WO-2015/043982 A1 | 4/2015 |
|---|---|---|

OTHER PUBLICATIONS

Thermo Scientific DyNAmo SYBR Green 2-Step qRT-PCR Kit Technical Manual, Thermoscientific Oct. 2011, p. 4, paragraph 2.
Quant-iT(TM) OliGreen ssDNA Reagent and Kit, Invitrogen, Nov. 20, 2008, pp. 1-2.
G. Tolun, A real-time DNase assay (ReDA) based on PicoGreen(R) fluorescence, Nucleic Acids Research, vol. 31, No. 18, Sep. 15, 2003, pp. 111-111.
I Blatta et al, Quantitative assay of total dsDNA with PicoGreen reagen and real-time fluorescent detection, 2005, pp. 119-123.
Singer, V. L. et al, Characterization of PicoGreen Reagent and Development of a Fluorescence-Based Solution assay for Double-Stranded DNA Quantitation Analyical Biochemistry, vol. 249, No. 2, Jul. 1, 1997, pp. 228-238.
Carsten Lundby et al, Gene expression human skeletal muscle: alternative normalization method and effect of repeated biopsies, European Journal of Applied Physiology, vol. 95, No. 4, Oct. 1, 2005, pp. 351-360.
Silprasit K et al., Simple and rapid determination of the enzyme kinetics of HIV-1 reverse transcriptase and anti-HIV-1 agents by a fluorescence based method, Journal of Virological Methods, vol. 171, No. 2, Feb. 1, 2011, pp. 381-387.
International Preliminary Report on Patentability dated Apr. 5, 2016 for International Application No. PCT/EP2014/069488, which was filed on Sep. 12, 2014 (Inventor—Nan Fang; Applicant—Qiagen GMBH) (6 Pages).
International Search Report dated Dec. 12, 2014 for International Application No. PCT/EP2014/069488, which was filed on Sep. 12, 2014 (Inventor—Nan Fang; Applicant—Qiagen GMBH) (6 Pages).
Written Opinion dated Dec. 12, 2014 for International Application No. PCT/EP2014/069488, which was filed on Sep. 12, 2014 (Inventor—Nan Fang; Applicant—Qiagen GMBH) (5 Pages).
Seville M, et al. "Fluorometric assay for DNA polymerases and reverse transcriptase", Biotechniques (1996) 21(4):664-672.
Communication pursuant to Article (94)3 EPC dated Apr. 19, 2017 by the European Patent Office for EP Application No. 14771238, which was filed on Sep. 12, 2014 and published as EP 3052643 A1 on Aug. 10, 2016 (Applicant—Qiagen GmbH) (6 pages).

* cited by examiner

*Primary Examiner* — Jezia Riley
(74) *Attorney, Agent, or Firm* — Ballard Spahr LLP

(57) ABSTRACT

The present invention relates to a method for real-time monitoring and/or quantification of newly-synthesized complementary deoxyribonucleic acid (cDNA) during a reverse transcription reaction of an ribonucleic acid (RNA) template in a sample, the method using a fluorogenic dye binding to RNA:cDNA hybrids. The present invention also relates to the use of this method as well as to kits employing the fluorogenic dye.

9 Claims, 4 Drawing Sheets

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: HIF-1A Forward Primer

<400> SEQUENCE: 1
ttacacacag aaatggcctt                                          20

<210> SEQ ID NO 2
<211> LENGTH: 22
<212> TYPE: DNA
<213> ORGANISM: Artificial Sequence
<220> FEATURE:
<223> OTHER INFORMATION: HIF-1A Reverse Primer

<400> SEQUENCE: 2
gaacattatt acagcagcca ga                                       22

<210> SEQ ID NO 3
<211> LENGTH: 17
<212> TYPE: DNA
<213> ORGANISM: Artificial Sequence
<220> FEATURE:
<223> OTHER INFORMATION: Myc Forward Primer

<400> SEQUENCE: 3
tgctccatga ggagaca                                             17

<210> SEQ ID NO 4
<211> LENGTH: 20
<212> TYPE: DNA
<213> ORGANISM: Artificial Sequence
<220> FEATURE:
<223> OTHER INFORMATION: Myc Reverse Primer

<400> SEQUENCE: 4
gtgatccaga ctctgacctt                                          20
```

QUANTIFICATION OF RNA

CROSS-REFERENCE TO RELATED APPLICATIONS

Figure 1A:
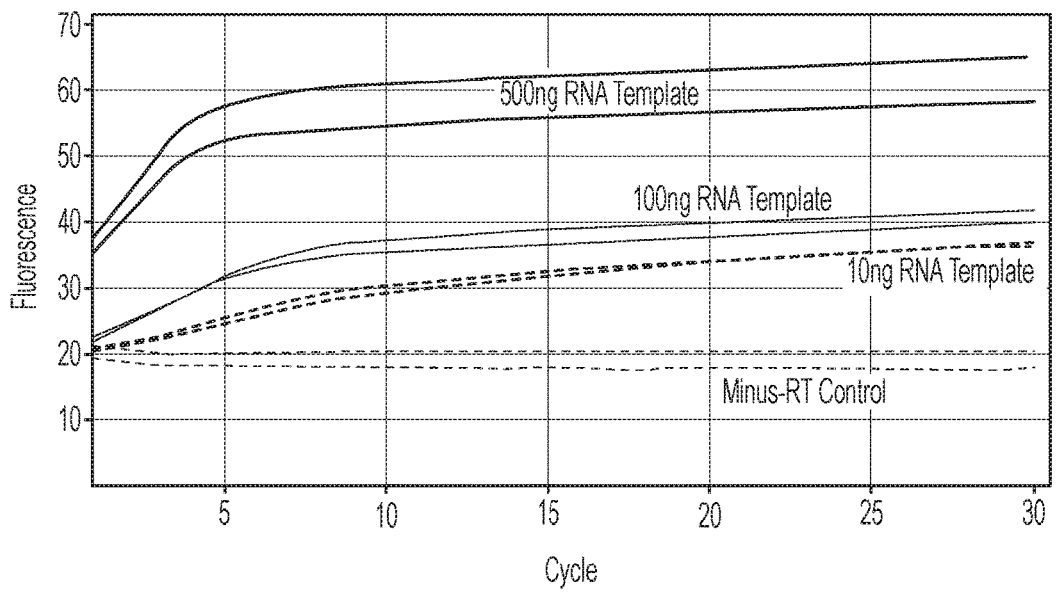

The present application is a U.S. National Stage Entry of PCT Application No. PCT/EP2014/069488, filed Sep. 12, 2014, which claims priority to EP Application No. 13186706.1, filed Sep. 30, 2013, both of which are hereby incorporated herein by their reference in their entirety.

REFERENCE TO SEQUENCE LISTING

The Sequence Listing submitted herein on Mar. 29, 2016, as a text file named "17104_0054U1_Sequence_Listing.txt," created on Mar. 29, 2016, and having a size of 931 bytes is hereby incorporated by reference pursuant to 37 C.F.R. §1.52(e)(5).

The present invention is directed to novel methods and kits and uses to be employed for the monitoring and/or quantification of newly-synthesized complementary deoxyribonucleic acid (cDNA) during a reverse transcription reaction of a ribonucleic acid (RNA) template in a sample.

FIELD OF THE INVENTION

The present invention relates to the field of molecular biology, more particularly to the generation and/or quantification of nucleic acids and, specifically, to the reverse transcription using an RNA-dependent-DNA polymerase, i.e. a reverse transcriptase, for the synthesis of cDNA from an RNA template.

BACKGROUND OF THE INVENTION

The quantification of nucleic acids represents an important tool in many molecular biology applications, such as gene expression analyses. A common approach to the study of gene expression is the production of complementary DNA (cDNA), the technique of which employs the reverse transcription of RNA into the complementary DNA using the enzyme reverse transcriptase (RT): In order to have the RNA transcribed, RNA molecules from an organism are isolated from an extract of the cells or tissues of the organism. By using the enzyme reverse transcriptase (RT) or a DNA polymerases having RT activity, cDNA copies may be created from the RNA template, which results in the production of single-stranded cDNA molecules. In the reverse transcription reaction primers, dNTPs, and a suitable buffer is commonly needed. The primers anneal to the RNA template and are extended on their 3'-end complementary to the RNA template. In order to prevent RNA from degradation, commonly RNase-inhibitors are employed increasing the reliability and reproducibility of the cDNA synthesis.

The discovery of the described reverse transcription reaction has enabled development of sensitive molecular biological methods not only for basic research, but also for the design of medicaments and diagnostics.

Known reverse transcriptases are the Avian myoblastosis virus (AMV) reverse transcriptase, which was the first widely used RNA dependent DNA polymerase. The enzyme has 5'-3' RNA dependent DNA polymerase activity, 5'-3' DNA dependent DNA polymerase activity, and RNase H activity. RNase H is a processive 5' and 3' ribonuclease specific for the RNA strand for RNA/DNA hybrids. Also, reverse transcriptase originating from Moloney murine leukemia virus (M-MLV) and from human immunodeficiency virus type 1 (HIV-1) are used extensively in molecular biology.

In general, reverse transcriptase is a multifunctional enzyme with at least three enzymatic functional activities: (i) RNA-dependent DNA-Polymerase, (ii) DNA-dependent DNA-Polymerase, and (iii) RNA-DNA-hybrid-dependent RNAse (RNase H).

The reverse transcription reaction primarily utilizes the RNA-dependent polymerase activity for the generation of cDNA. This activity permits the in-vitro synthesis of cDNA for cloning and reverse transcriptase polymerase chain reactions, RNA-sequencing and primer extension experiments. Also, with this activity, an RNA template can only transcribed into one molecule of cDNA, and there is no amplification during the reverse transcription of the RNA sequence.

The RNase H activity specifically recognizes and degrades RNA:DNA hybrids. Thus, this activity does not affect pure RNA, but only RNA hybridized to the newly-synthesized cDNA. As a consequence, the RNA can be degraded by the RNase H only as early as the cDNA has been synthesized. Some of the reverse transcriptases presently available on the market have been mutated and have, thus, no significant RNase H activity. In case such RNase H deficient reverse transcriptases are being employed in reverse transcription reactions, and in case the cDNA generated in the reverse transcription reaction is, e.g, to be used for RT-PCR, a separate RNA-degradation step following reverse transcription reaction has to be performed by incubation with RNase H.

With the single-stranded cDNA as template, the DNA-dependent DNA polymerase activity synthesizes a complete double-stranded cDNA of the original mRNA. It is noted, however, that a premature synthesis of the second strand often leads to shortened double-stranded cDNAs, since—after uncompleted transcription—the reverse transcription reaction activity for the single-strand synthesis often switches into the second-strand synthesis activity. Thus, in the recent in-vitro reaction conditions the double-stranded cDNA-synthesis of the reverse transcriptase is usually suppressed.

The cDNA generated in the reverse transcriptase reaction can then be further characterized and quantified by methods such as cloning, sequencing, and polymerase chain reaction (PCR); the latter, i.e. PCR, exploits first-strand cDNA for mRNA sequence(s) as template for amplification by the PCR. This method is referred to as reverse transcriptase PCR (RT-PCR), which method is widely used for detection and quantification of RNA.

Ideally, the reverse transcription reaction synthesizing the cDNA—completely representing the applied RNA—should be unaffected by interfering factors whatsoever, and should, thus, represent a non-biased reaction. In reality, however, the efficiency of the reverse transcriptase reaction can vary greatly, depending on factors such as the intrinsic enzymatic properties of the reverse transcriptase, reaction buffer composition, reaction temperature and duration, and possible reverse transcriptase inhibitors present in the RNA sample to assess. All these factors may negatively affect the reverse transcriptase efficiency and may lead to shortened cDNA-molecules, consequently leading to a direct impact on the outcome of downstream analyses such as sequencing and PCR.

Although several different approaches have been made to improve overall efficiency of the reverse transcription conditions and, thus, of the cDNA synthesis as such, today, there still is the need for effectively optimizing the reverse transcriptase, buffers, temperature and other conditions, in particular when developing new reverse transcriptase products.

In view of the above, it is an object of the present invention to provide for tools by means of which reliable and reproducible information on reverse transcriptase kinetics and reverse transcription efficiency can be gained.

The present invention satisfies these and other needs.

SUMMARY OF THE INVENTION

The present invention provides methods and kits for real-time monitoring and/or quantification of newly-synthesized complementary deoxyribonucleic acid (cDNA) during a reverse transcription reaction of an ribonucleic acid (RNA) template in a sample, the method comprising the steps of:
(ii) providing a sample comprising said RNA template;
(ii) contacting said sample with a) a reverse transcriptase, and b) a fluorogenic dye recognizing RNA:cDNA hybrids with higher affinity than RNA molecules alone;
(iii) reverse transcribing said RNA template under conditions permissive for the production cDNA and of the generation of double-stranded RNA/cDNA hybrids, whereby the fluorogenic dye binds to said forming RNA:cDNA hybrids; and
(iv) measuring fluorescence of said fluorescent dye during the reverse transcription reaction, thereby monitoring and/or quantifying the newly-synthesized cDNA.

In a preferred embodiment, a fluorogenic dye is employed that specifically recognizes and binds to RNA:cDNA hybrids.

Herein and as generally understood in the respective field, a "fluorogenic dye" is intended to mean as a colored substance or colourant, in particular one that has an affinity to the substrate to which it is being applied and that is able to generate fluorescence.

Presently, and as generally understood, the expression "a fluorogenic dye recognizing RNA:cDNA hybrids with higher affinity than RNA molecules alone" shall mean that the dye to be employed can also bind to, e.g., dsDNA to some extend but, however, binds with a higher affinity to RNA:DNA hybrids and shows higher fluorescence if bound to RNA:DNA hybrids compared to if bound to RNA molecules alone. Accordingly, "a fluorogenic dye recognizing RNA:cDNA hybrids" is intended to mean a colored substance being able to a) bind to RNA/DNA hybrids and b) generate fluorescence upon binding thereupon, and "with higher affinity than RNA molecules alone" shall mean that the fluorogenic dye to be employed binds to and forms a complex with RNA/cDNA hybrids with a greater intermolecular force compared to the dye's binding to an RNA molecule alone.

Accordingly, the term a "fluorogenic dye specifically recognizing RNA/cDNA hybrids" as used herein is intended to mean a colored substance being able to a) specifically bind to RNA/DNA hybrids and b) generate fluorescence upon binding thereupon.

Also, the term "binding" to a RNA:cDNA hybrid as used herein is intended to mean any form of binding, and shall also comprise intercalating, i.e. the (reversible) inclusion of the dye between the RNA strand and the cDNA strand. Preferably, the dye does not lead to functional changes, and does not inhibit subsequent replication/amplification or other processes applied after the reverse transcription reaction.

An "RNA:cDNA hybrid" is commonly understood as an RNA template being annealed to its complementary DNA strand, the latter of which is newly synthesized during reverse transcription of the RNA template.

The expression "real time monitoring and/or quantifying" in connection with/during the reverse transcription reaction as used herein, is intended to mean that while the RNA is transcribed into cDNA a simultaneous quantification of the thereby generated RNA:cDNA hybrids takes place. Thus, besides detection of the RNA:cDNA hybrids, also quantification is enabled.

Thus, according to the method of the invention the fluorogenic dye is present in the reaction at least as early as the reverse transcriptase reaction is started. This means that fluorogenic dye may be added prior to the addition of the reverse transcriptase to the sample or simultaneously, or even after the reverse transcriptase is added to the sample, however, in each case the reverse transcriptase reaction is only started if the both, the reverse transcriptase and the fluorogenic dye are present in the sample the reaction is to be performed upon.

According to the invention, the fluorogenic dye specifically intercalates or otherwise binds to the RNA:cDNA hybrids generated during transcription of the RNA template, and the binding/intercalation of the fluorogenic dye leads to the generation of RNA:cDNA-fluorogenic-dye-complexes that, upon excitation, emit light at a certain wave length, which can then be measured during the reverse transcription reaction.

Thus, via the measurement of the emitted light during the reverse transcriptase reaction, the formation of the RNA:cDNA-hybrids and, as a prerequisite to that, the generation of cDNA may be monitored and quantified in real time, i.e. with the generation of the cDNA during the reverse transcriptase reaction.

The method according to the invention, thus, allows direct monitoring of a reverse transcription reaction in real time and determining its kinetics and efficiency, which is of high importance since the efficiency of a reverse transcription reaction directly impacts downstream applications: For example, in the applications where mRNA or viral RNA is first reverse-transcribed to cDNA and then quantified by quantitative PCR (qPCR), the detection sensitivity and quantification accuracy are closely connected to reverse transcription efficiency. Without the method according to the invention, additional experiments, commonly either optical density (OD) measurement or qPCR, were/are needed to quantify cDNA molecules, the fact of which introduces several undesirable drawbacks. First, it is tedious and time-consuming. For example, OD measurement of cDNA yield requires purification of the cDNA from the RT reaction to remove components that could possibly alter the OD values. Second, the quantification of cDNA by PCR is influenced by factors such as PCR primer design and PCR master mix compositions, and reflects not only reverse transcription but also PCR efficiency. Third, PCR can only be used to quantify selected cDNAs and does not necessarily reflect the total cDNA synthesize from the mixed RNA template in an RT reaction.

Thus, with the method according to the invention the above-mentioned problems in determining RT efficiency can be overcome: the efficiency of a reverse transcription reaction can be assessed, i.e. how much cDNA can be successfully generated from a given amount of an RNA template.

By means of the novel method, different factors determining the reverse transcription efficiency can be assessed and compared such as the activity and processivity of a reverse transcriptase, buffer composition, types and concentrations of the reverse transcription primers, reaction temperature and duration, and the quality of the RNA template.

A "sample" is anything containing RNA or mRNA. The test sample is or can be derived from any biological source or of any origin, e.g., viral, bacterial, archaebacterial, fungal, ribosomal, prokaryotic or eukaryotic, human, animal, plant, microorganisms, etc. It may be a sample of any organism, tissue, cell or sub-cellular compartment. The test sample can be used either (i) directly as obtained from the source or origin, or (ii) following a pre-treatment of the sample, such as isolation, purification or modification. Also, artificial RNAs may be quantified. The length of the RNAs may vary. The RNAs may be modified, e.g. may comprise one or more modified nucleobases or modified sugar moieties (e.g. comprising methoxy groups).

As mentioned before, with the method according to the invention, the efficiency of the reverse transcriptase may be assessed and—in view of the outcomes—optimized: Thus, with the method according to the invention, different factors influencing the efficiency of a reverse transcription reaction may be assessed, such as the efficiency of a certain reverse transcriptase on an RNA template, e.g. compared to another reverse transcriptase; buffer composition; reaction duration and temperature; types and concentration of primers; and quality of the RNA template.

According to a preferred embodiment of the method according to the invention, the fluorogenic dye is selected from at least one or more of the following: [2-[N-bis-(3-dimethylaminopropyl)-amino]-4-[2,3-dihydro-3-methyl-(benzo-1,3-thiazol-2-yl)-methylidene]-1-phenyl-quinolinium]$^+$; 4',6-diamidino-2-phenylindole; bisbenzimide dyes; OliGreen®; Cyanine Dyes including TOTO® and YOYO® family of dyes, ethidium bromide, and Sybr Green; anthraquinone dye, in particular DRAQ5; and/or functional derivatives or analogues thereof.

The fluorogenic cyanine dye 2-[N-bis-(3-dimethylaminopropyl)-amino]-4-[2,3-dihydro-3-methyl-(benzo-1,3-thiazol-2-yl)-methylidene]-1-phenyl-quinolinium$^+$ is also commonly designated as PicoGreen, and represents a fluorescent probe that, in a sample containing single-stranded nucleic acid molecules, such as RNA and single-stranded DNA molecules, as well as double-stranded nucleic molecules, specifically binds to the double-stranded molecules, which represent in the case of reverse transcription, RNA:cDNA hybrids. This dye forms a highly luminescent complex upon binding to the DNA when compared to the unbound/free dye in solution, with significantly increased fluorescence intensity.

PicoGreen, Sybr Green, and OliGreen® are commercially available from different companies, such as Life Technologies (Invitrogen, USA). DRAQ5 is available, e.g. from eBiosciences, USA.

Herein, the expression "functional derivatives thereof" in connection with the fluorogenic dyes mentioned above, e.g. 2-[N-bis-(3-dimethylaminopropyl)-amino]-4-[2,3-dihydro-3-methyl-(benzo-1,3-thiazol-2-yl)-methylidene]-1-phenyl-quinolinium]$^+$ is understood as to comprise compounds which have a chemical structure directly derived from the respective fluorogenic dye, e.g. 2-[N-bis-(3-dimethylaminopropyl)-amino]-4-[2,3-dihydro-3-methyl-(benzo-1,3-thiazol-2-yl)-methylidene]-1-phenyl-quinolinium]+ and which exhibit biological/physical and/or (bio)chemical properties similar to those of the respective fluorogenic dye, e.g. 2-[N-bis-(3-dimethylaminopropyl)-amino]-4-[2,3-dihydro-3-methyl-(benzo-1,3-thiazol-2-yl)-methylidene]-1-phenyl-quinolinium]+, in particular the RNA:cDNA binding/intercalating properties of 2-[N-bis-(3-dimethylaminopropyl)-amino]-4-[2,3-dihydro-3-methyl-(benzo-1,3-thiazol-2-yl)-methylidene]-1-phenyl-quinolinium]$^+$ and the fluorescence properties.

Similarly, the expression "functional analogues thereof in connection with the fluorogenic dyes mentioned above, e.g. 2-[N-bis-(3-dimethylaminopropyl)-amino]-4-[2,3-dihydro-3-methyl-(benzo-1,3-thiazol-2-yl)-methylidene]-1-phenyl-quinolinium]+ is understood as to comprise compounds which have a chemical structure directly derived from the respective fluorogenic dye, e.g. 2-[N-bis-(3-dimethylaminopropyl)-amino]-4-[2,3-dihydro-3-methyl-(benzo-1,3-thiazol-2-yl)-methylidene]-1-phenyl-quinolinium]+ and which exhibit biological/physical and/or (bio)chemical properties similar to those of the respective fluorogenic dye, e.g. 2-[N-bis-(3-dimethylaminopropyl)-amino]-4-[2,3-dihydro-3-methyl-(benzo-1,3-thiazol-2-yl)-methylidene]-1-phenyl-quinolinium]+, in particular the RNA:cDNA binding/intercalating properties of 2-[N-bis-(3-dimethylaminopropyl)-amino]-4-[2,3-dihydro-3-methyl-(benzo-1,3-thiazol-2-yl)-methylidene]-1-phenyl-quinolinium]$^+$ and the fluorescence properties.

The TOTO® and YOYO® family of dyes represents dimeric cyanine dyes that belong to the class of cyanine dyes, which also includes ethidium bromide and Sybr Green, all of which are employed in molecular biology.

According to another aspect of the invention, the sample is a total RNA preparation sample or a poly(A)+ sample. A total RNA preparation contains, besides mRNA characterized by a polyA, also tRNA and rRNA. A poly(A)+ RNA sample can be prepared by isolating poly(A)+ from a total RNA preparation, e.g. by a single run on oligo(dT)-column (see, e.g., Sambrook et al., Molecular Cloning: A Laboratory Manual, Cold Spring Harbor Laboratory Press, Cold Spring Harbor, N.Y., 1989).

"Total RNA preparation", as used herein, is intended to mean a preparation containing all RNA that may be present in a test sample. In other words, nucleic acid sequences made up of ribonucleotide monomers which may include, for example, genomic RNA, subgenomic RNA fragments, mRNA, transfer RNA (tRNA) and ribosomal RNA (rRNA). A total RNA preparation may also comprise nucleic acid sequences made up of deoxyribonucleotide monomers including, for example, genomic DNA, subgenomic DNA fragments and products from DNA amplification reactions.

According to another aspect of the invention, from 1 ng to 2000 ng RNA, preferably from 10 ng to 1000 ng RNA template is used. Within the context of this invention it has been found that the method according to the invention can be performed with the mentioned amounts.

According to a preferred embodiment of the method according to the invention, the reverse transcriptase (RT) is selected from the group of Omniscript-RT, Sensiscript-RT (Qiagen), AMV-RT, M-MLV-RT, HIV-RT, EIAV-RT, RAV2-RT, SuperScript-RT (LIFE Technologies), Monsterscript (Epicentre), ThermoScript and Thermo-X (Invitrogen), *Thermus thermophilus* DNA polymerase I, and/or functional variants or derivatives thereof. The enzyme may also have increased fidelity like e.g. AccuScript reverse Transcriptase (Stratagene). A skilled person knows that one or more suitable enzyme with reverse transcriptase activity can be mixed to gain optimized conditions or novel features. It is to be understood that also mixtures of these may be applied with the method according to the invention, as well as mixtures of reverse transcriptase with thermophilic enzymes, or an enzyme having RNase H activity and an enzyme being RNase H negative, or an enzyme with increased fidelity and a thermophilic enzyme. Numerous other combinations are possible based on the list of preferred enzymes having reverse transcriptase activity in the scope of the invention.

Preferably, the method is carried out in one reaction vessel, which means that the sample to be tested and containing the RNA is contacted with the RNA transcriptase and the fluorogenic dye in the vessel the reverse transcription reaction and the formation of RNA:cDNA hybrids and the binding of the fluorogenic dye to the RNA:cDNA hybrids takes place.

The method according to the invention may be performed in any apparatus comprising an optical system suitable for detecting fluorescent molecule concentrations, i.e. for fluorescence analyses. Such an apparatus represents a fluorometer by means of which parameters of fluorescence, i.e. intensity and wavelength distribution of emission spectrum after excitation by a certain spectrum of light, can be measured.

The apparatus comprising the optical system is preferably combined with a block heater element being able to incubate tubes containing a sample to be assayed at a constant or variant temperature. Also, any PCR cycler with suitable thermal and optical performance can be used.

According to another aspect of the invention, fluorescence is measured at various time points during the reverse transcriptase reaction. In this embodiment it is preferred if the fluorescence is measured every 10, 20, 30, 40, 50, or 60 seconds, and preferably every 30 seconds.

The invention further relates to a kit for the quantification of cDNA synthesis, the kit comprising
(i) at least one reverse transcriptase, and
(ii) a fluorogenic dye recognizing RNA:cDNA hybrids with higher affinity than RNA molecules alone, in particular a fluorogenic dye specifically recognizing and binding to RNA/cDNA hybrids.

Preferably, the fluorogenic dye is selected from at least one or more of the following: [2-[N-bis-(3-dimethylaminopropyl)-amino]-4-[2,3-dihydro-3-methyl-(benzo-1,3-thiazol-2-yl)-methylidene]-1-phenyl-quinolinium]+; 4',6-diamidino-2-phenylindole; bisbenzimide dyes; OliGreen®; Cyanine Dyes including TOTO® and YOYO® family of dyes, ethidium bromide, and Sybr Green; anthraquinone dye, in particular DRAQ5; or functional derivatives and/or analogues thereof.

As for the method above, the reverse transcriptase (RT) that can be contained in the kit according to the invention can be selected from the group of Omniscript-RT, Sensiscript-RT (Qiagen), AMV-RT, M-MLV-RT, HIV-RT, EIAV-RT, RAV2-RT, Super-Script-RT (LIFE Technologies), Monsterscript (Epicentre), ThermoScript and Thermo-X (Invitrogen), *Thermus thermophilus* DNA polymerase I, and/or functional variants or derivatives thereof. The kit may also contain more than one, e.g. two, three or four or more different reverse transcriptases, as well as more than one of the fluorogenic dyes specifically recognizing and binding RNA/cDNA hybrids.

With the kit according to the invention a tool is provided by means of which the efficiency of different reverse transcription conditions in view of a certain RNA sample can be assessed. The conditions may comprise the efficiency of a reverse transcriptase on an RNA template, different buffer composition, reaction duration and temperature, types and concentration of primers, quality of the RNA template.

According to a preferred embodiment of the kit according to the invention, the kit further comprises at least one or more of the following: a buffer for elimination of genomic DNA from a RNA template containing sample, a reverse transcriptase buffer, RNase inhibitor, oligo-dT primer, random primer, gene specific primer, RNase-free water.

The kit may also comprise a manual for performing the method according to the invention as outlined above.

The invention also relates to the use of a fluorogenic dye specifically recognizing and binding to RNA:cDNA hybrids during a reverse transcriptase reaction for monitoring and/or quantifying real-time cDNA synthesis from an RNA template.

In a preferred embodiment, the fluorogenic dye is selected from at least one or more of the following: [2-[N-bis-(3-dimethylaminopropyl)-amino]-4-[2,3-dihydro-3-methyl-(benzo-1,3-thiazol-2-yl)-methylidene]-1-phenyl-quinolinium]+; 4',6-diamidino-2-phenylindole; bisbenzimide dyes; OliGreen®; Cyanine Dyes including TOTO® and YOYO® family of dyes, ethidium bromide, and Sybr Green; anthraquinone dye, in particular DRAQ5; or functional derivatives and/or analogues thereof.

The invention further relates to the use of the method according to the invention and as outlined above for determination of the efficiency and/or reaction kinetics of a reverse transcriptase reaction, wherein preferably at least one of the following is determined: activity and/or processivity of one or more reverse transcriptase, reverse transcription reaction buffer conditions, types and/or concentrations of primers used for the reverse transcription reaction of an RNA, reverse transcription reaction temperature and/or duration, and/or quality of an RNA template.

Unless defined otherwise, all technical and scientific terms used herein generally have the same meaning as commonly understood by one of ordinary skill in the art to which this invention belongs.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

Figure 2A:
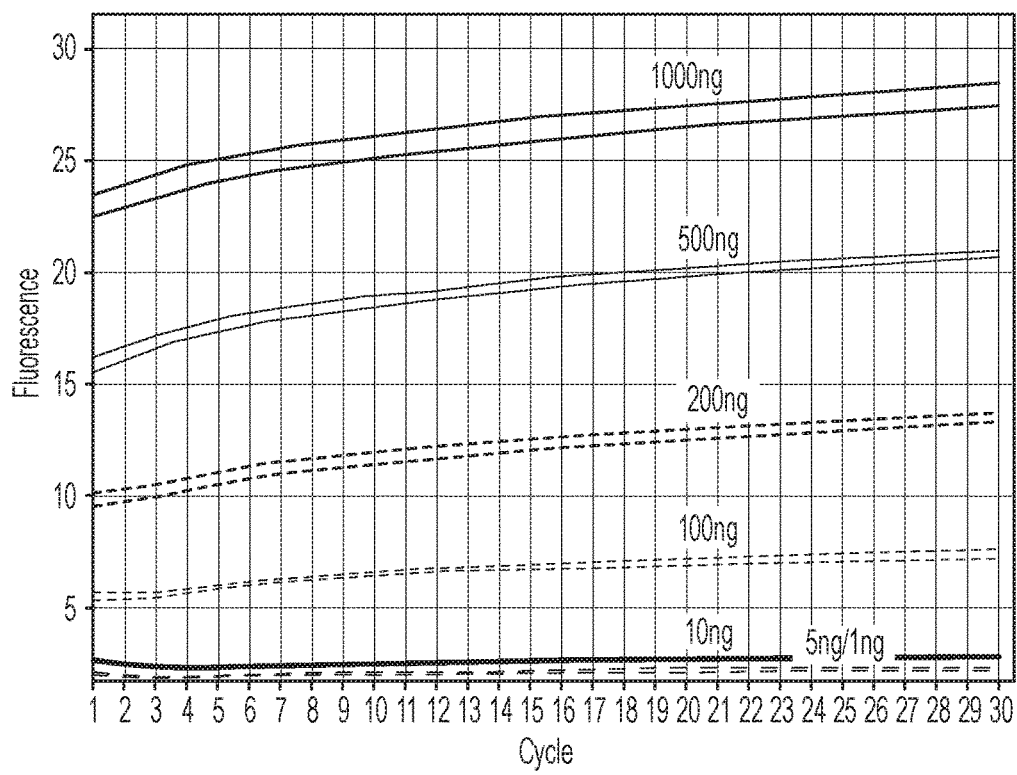
Figure 2B:
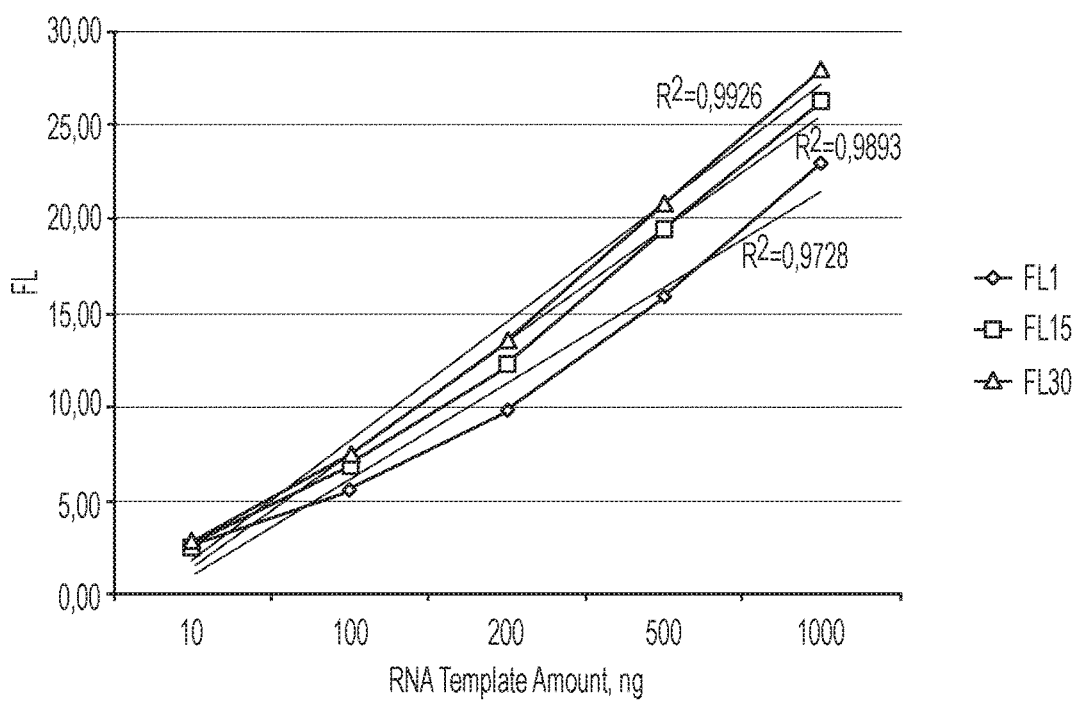
Figure 3A:
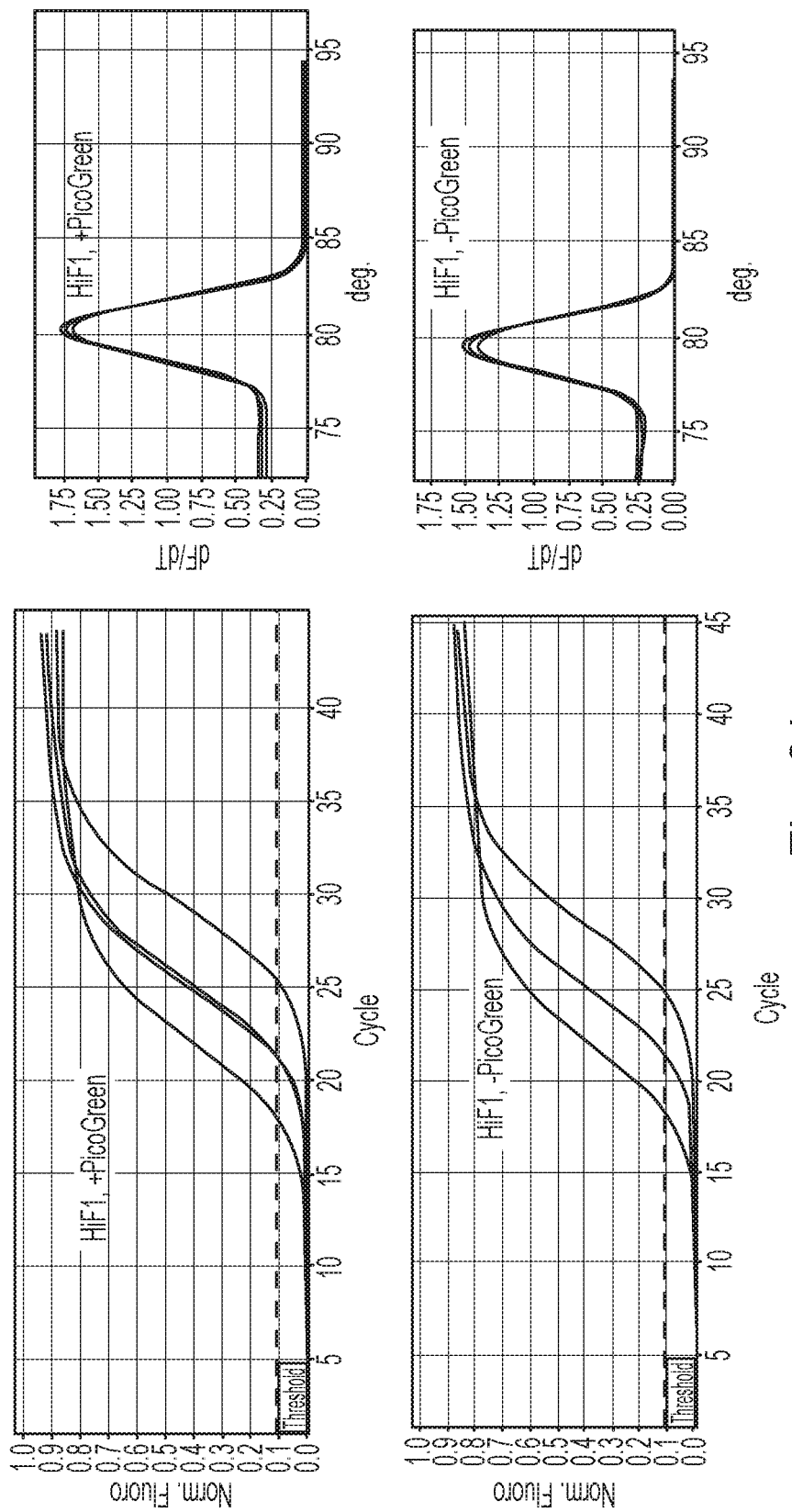
Figure 3B:
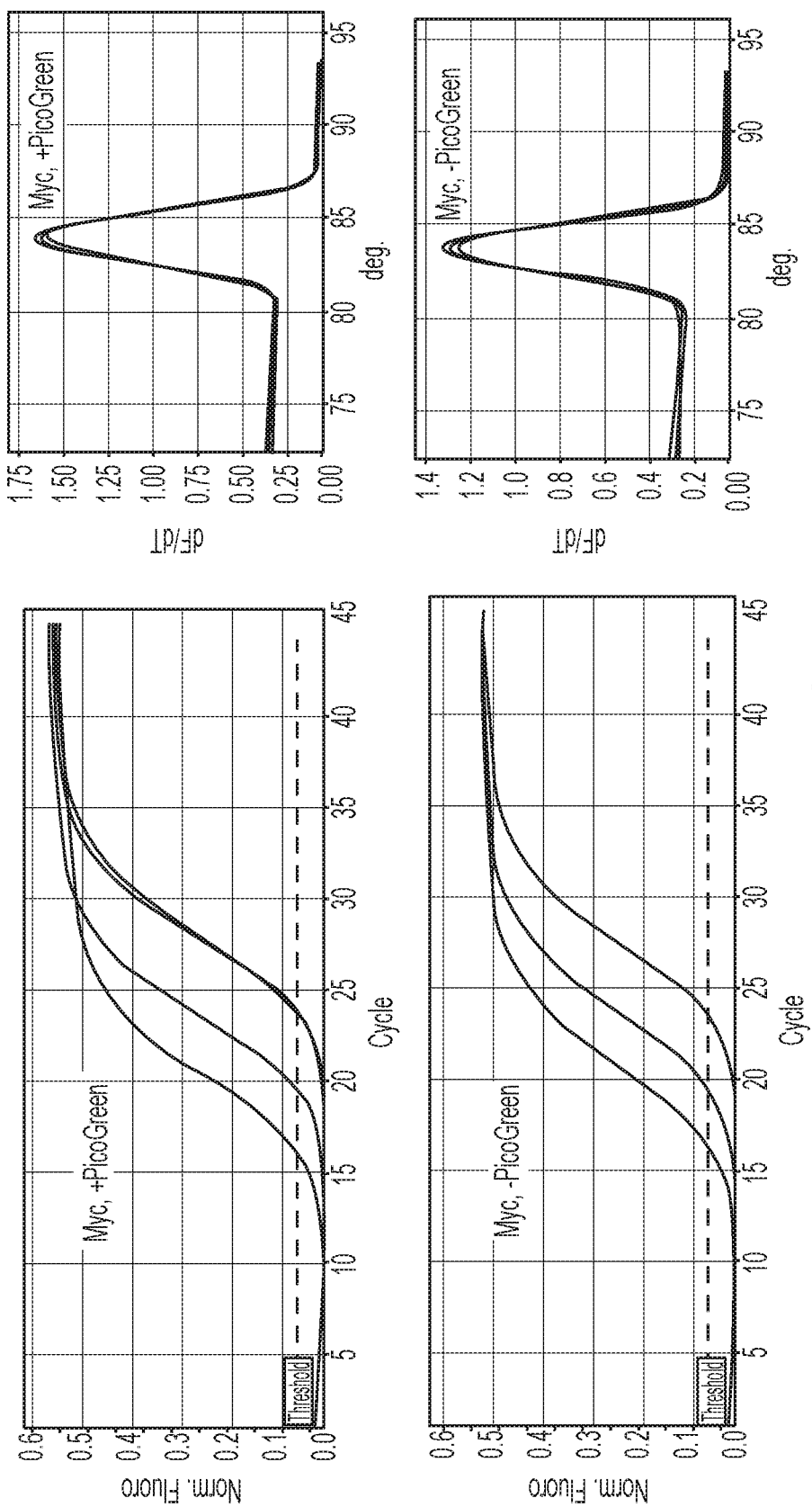

Several embodiments of the invention are illustrated in the figures and explained in more detail in the following description. In the figures:

FIG. 1 shows diagrams displaying fluorescent measurement curves for different amounts RNA templates in reverse transcription reactions using Quantiscript reverse transcriptase (Qiagen) was used (A), or Superscript reverse transcriptase (Life Technologies) (B), mixed with PicoGreen, respectively; the reverse transcriptase reaction was performed in a Rotorgene Q Cycler (Qiagen) at 42° C. for 14 minutes; the fluorescence signals generated from the fluorogenic dye PicoGreen were collected in the Green channel every 30 seconds;

FIG. 2 shows diagrams displaying the real-time detection of cDNA generated with different RNA template amounts (between 1 ng and 1000 ng) that were reverse transcribed with Quantiscript reverse transcriptase (Qiagen) (A); in (B) the correlation between the fluorescence intensity at various time points and RNA template amounts is shown, plotting the diagrams with fluorescence levels (FLs) on Y-axis and RNA amount (ng, from 10 ng to 1000 ng) on X-axis; and FIG. 3 shows amplification curves and melting curves in a downstream quantitative PCR (qPCR) analysis, which was performed after the reverse transcription reaction employing PicoGreen; different amounts of HeLa RNA were reverse-transcribed with Quantiscript reverse transcriptase (Qiagen), either in the presence or absences of the fluorogenic dye PicoGreen; subsequently, 1 μl of the reverse transcription product was used as template for qPCR using gene-specific primers for HIF-1A (A) or Myc (B); amplification curves are shown on the left hand side, the melting curves on the right hand side, respectively, with PicoGreen (+PicoGreen) in the reverse transcriptase reaction, and without PicoGreen (−PicoGreen) in the reverse transcriptase reaction, respectively.

EXAMPLES

With the present invention, an easy and straightforward method to directly monitor reverse transcriptase reaction in real time was developed. As an exemplary fluorogenic dye to be employed in the method, kits and uses according to the invention, the fluorogenic dye PicoGreen was chosen for its ability to selectively detect DNA:RNA hybrid in the presence of ssDNA and RNA.

In first experiments it was tested whether PicoGreen can detect cDNA in real time with the standard reverse transcription procedure of the QuantiTect Reverse Transcription kit (QIAGEN): Different amounts of total cellular RNA exacted from cultured HeLa cell line (10 ng, 10 ng, and 500 ng) were first treated with genomic DNA (gDNA) Wipeout buffer at 42° C. for 2 minutes to remove gDNA, and then mixed with all reverse transcription reaction components provided in the kit (Quantiscript Reverse Transcriptase, Quantiscript RT Buffer, RT Primer Mix, RNase-free water) following the manufacturer's instructions, as well as PicoGreen (LIFE Technologies) at 1× final concentration. A minus-RT control was also included where 500 ng HeLa RNA was mixed with all RT reaction components except Quantiscript Reverse Transcriptase. The RT reaction was then performed in duplicates on a Rotorgene Q cycler (QIAGEN) at 42° C. for 15 minutes. The fluorescence signals generated from PicoGreen were collected in the Green channel every 30 seconds.

As shown in FIG. 1A, an increase of PicoGreen signals can be clearly detected in the RT reactions, indicating the accumulation of the newly synthesized cDNA. The RT reactions with 10 ng, 100 ng, and 500 ng RNA templates show similar kinetics: the most rapid fluorescence increase was observed between 0 and 5 minutes; afterwards, the reaction gradually entered into plateau phase. The absolute fluorescence levels (FLs) positively correlate with the starting RNA template amounts. In contrast, no increase of fluorescence signal was observed in the minus-RT control.

In an additional experiment, PicoGreen was used to detect cDNA synthesis in real time with another reverse transcriptase, the SuperScript Vilo cDNA Synthesis Kit (LIFE Technologies), which uses an engineered version of M-MLV RT. The RT reaction was performed in duplicates on a Rotorgene Q cycler following manufacturer's instructions. Briefly, 10 ng, 100 ng, or 1000 ng HeLa RNA was combined with VILO Reaction Mix, SuperScript Enzyme Mix, PicoGreen (1× final concentration), and RNase-free water to a final volume of 20 µl. A minus-RT control was included where 1000 ng HeLa RNA was mixed with PicoGreen and all RT reaction components except SuperScript Enzyme Mix. The reaction mixes were first incubated at 25° C. for 10 minutes and then at 42° C. for 60 minutes, the fluorescence signals generated from PicoGreen were collected at 42° C. in the Green channel every 30 seconds.

Figure 1B:
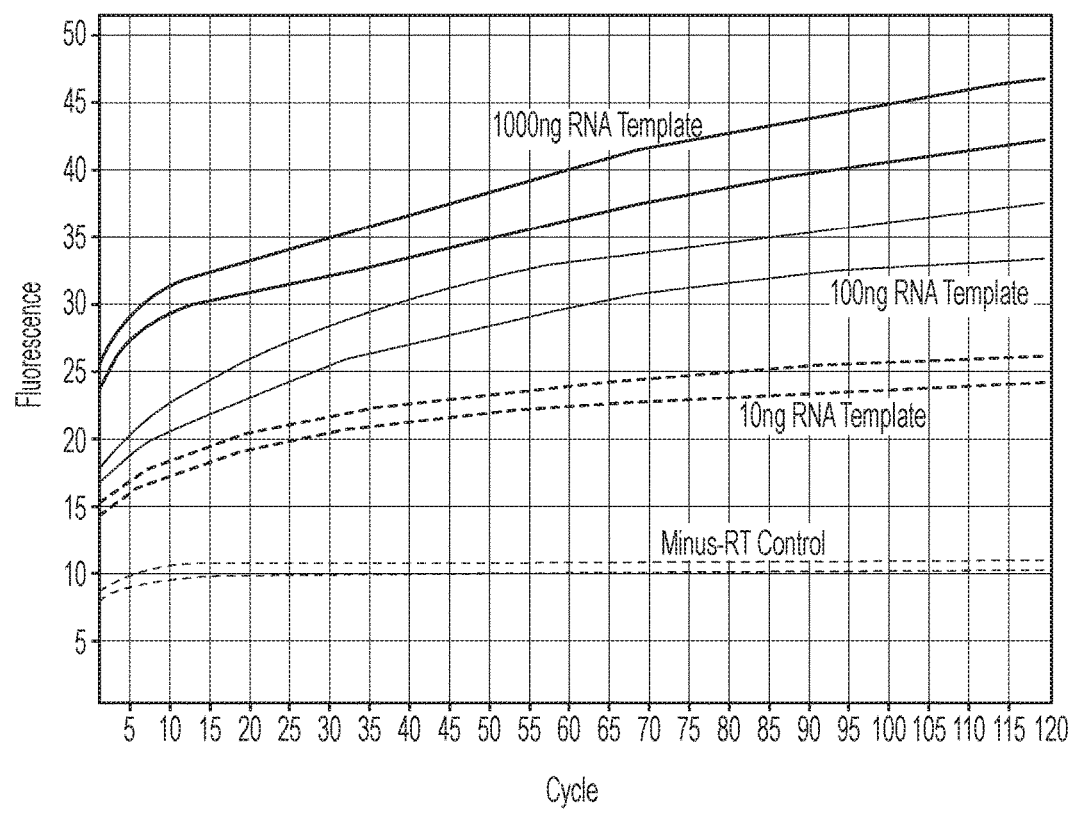

As shown in FIG. 1B, a steady increase of the fluorescence signals was observed in all RT reactions with SuperScript Enzyme Mix, but not in the minus-RT control. As expected, the absolute fluorescence levels (FLs), positively correlate with the starting RNA template amounts. Thus, also the SuperScript reverse transcriptase proved to be suitable in the method and uses according to the present invention, although RT reaction kinetics was somewhat different from that with the QuantiTect Reverse Transcription kit. For example, the RT with 100 ng RNA template began to enter into plateau phase after about 5 minutes (FIG. 1A, X-axis, time point 10) with the QuantiTect Reverse Transcription, while the RT product from 100 ng RNA template kept accumulating throughout the whole RT duration of 60 minutes with the SuperScript Vilo cDNA Synthesis Kit (FIG. 1B).

To test the detection limit and linear range of the method, different amounts of the HeLa RNA, ranging from 1 ng to 1000 ng (1 ng, 5 ng, 10 ng, 100 ng, 200 ng, 500 ng, 1 µg), were reverse transcribed to cDNA with the QuantiTect Reverse Transcription kit. All RT reactions were performed in duplicates according to manufacturer's instructions.

As shown in FIG. 2A, the RT reactions with 1 ng and 5 ng RNA template both generated low fluorescence signals that are barely above the background, suggesting that both template amounts were likely either close to or below the detection/quantification limit of the method. However, the fluorescence curves of the RT reactions with 10 ng to 1000 ng RNA template could be readily detected and also clearly distinguished from one another.

Next, the correlation between fluorescence intensity at various time points and RNA template amounts were examined. The fluorescence levels (FLs) at time points 1, 15, and 30, which correspond to 0.5 min, 7.5 min, and 15 min after the start of the RT reaction, were summarized in Table 1.

TABLE 1

Correlation of fluorescence level (FL) and RNA template amounts.

| RNA, ng | FL1, Mean | FL15, Mean | FL30, Mean |
| --- | --- | --- | --- |
| 1 | 1.86 | 2.15 | 2.29 |
| 5 | 2.08 | 2.21 | 2.35 |
| 10 | 2.57 | 2.61 | 2.79 |
| 100 | 5.57 | 6.83 | 7.43 |
| 200 | 9.77 | 12.27 | 13.51 |
| 500 | 15.87 | 19.41 | 20.80 |
| 1000 | 22.97 | 26.33 | 27.93 |

Diagrams with FLs on Y-axis and RNA amount (ng) on X-axis are shown in FIG. 2B. The coefficient of determination values, R2, were 0.9728, 0.9893, and 0.9926 for time points 1, 15, and 30, respectively. Assuming the same RT efficiency regardless of the template amounts, the data suggested that the fluorescence signals at different time points, from 30 seconds to 15 minutes after RT reaction start, correlate well with the cDNA generated during the RT reaction.

It was also tested whether PicoGreen in the RT reaction could negatively impact RT or downstream quantitative polymerase chain reaction (qPCR) (FIG. 3 and Table 2). Different amounts of HeLa RNA (10 ng, 100 ng, and 1 µg) were reverse-transcribed with QuantiTect Reverse Transcription kit in the presence or absence of PicoGreen. After the RT, 1 µl of each cDNA was used as template in a 25 µl qPCR reaction using QuantiFast Sybr Green PCR Mix (QIAGEN) and primers specifically detecting either HIF-1 (Sequences 1 and 2) or myc genes (Sequences 3 and 4): Sequence 1: HIF-1A Forward: TTACACACAGAAATG-GCCTT (SEQ ID No. 1); Sequence 2: HIF-1A Reverse: GAACATTATTACAGCAGCCAGA (SEQ ID No. 2); Sequence 3: Myc Forward: TGCTCCATGAGGAGACA (SEQ ID No. 3); Sequence 4: Myc Reverse: GTGATCCA-GACTCTGACCTT (SEQ ID No. 4).

As demonstrated by the Ct comparison in Table 2, the presence of PicoGreen did not have any significant impact on the Ct values (Ct=threshold cycle, i.e. the number of cycles at which the fluorescence exceeds the threshold). Furthermore, the melting temperatures of the PCR products were also not altered; the green fluorescence signal intensity was only slightly increased with cDNA template generated in the presence of the PicoGreen, possibly due to the interaction of residual PicoGreen and PCR products.

TABLE 2 qPCR was not affected by PicoGreen in the RT. The mean Ct values of the qPCR are summarized in Table 2.

|  | Ct Mean, With PicoGreen | Ct Mean, Without PicoGreen |
| --- | --- | --- |
| HIF-1A |  |  |
| 1000 ng | 17.26 | 17.16 |
| 100 ng | 20.37 | 20.41 |
| 10 ng | 24.52 | 23.85 |
| Myc |  |  |
| 1000 ng | 14.94 | 14.96 |
| 100 ng | 18.09 | 17.98 |
| 10 ng | 22.41 | 21.71 |

Taken together, with the above experiments and data the use of a convenient fluorescence-based method to directly monitor cDNA synthesis in real-time during RT reaction was demonstrated. It was also demonstrated that the addition of fluorescence dye PicoGreen in the RT reaction does not have significant impact on the cDNA synthesis and qPCR. Thus, It is also possible to use this method in combination with quantification standards (for example, double-stranded DNA or DNA:RNA hybrid with pre-defined concentrations) for absolute quantification of the cDNA in real-time.

The method and its use according to the invention may be employed, e.g., for optimization of reverse transcriptase enzymes and/or reaction chemistry.

Moreover, the kits and methods according to the invention can also be used as a simple and direct reverse transcription efficiency control.

The invention claimed is:

1. A method for real-time monitoring and quantification of newly-synthesized complementary deoxyribonucleic acid (cDNA) during a reverse transcription reaction of a ribonucleic acid (RNA) template in a sample, the method comprising the steps of:
    (i) providing a sample comprising said RNA template;
    (ii) contacting said sample with a) a reverse transcriptase, and b) a fluorogenic dye that binds to RNA/cDNA hybrids with higher affinity than RNA molecules alone;
    (iii) reverse transcribing said RNA template under conditions permissive for the production cDNA and of the generation of double-stranded RNA/cDNA hybrids, whereby the fluorogenic dye binds to said forming RNA/cDNA hybrids; and
    (iv) measuring fluorescence of said fluorescent dye during the reverse transcription reaction, thereby monitoring and quantifying the newly-synthesized cDNA.

2. The method of claim 1, characterized in that the fluorogenic dye is selected from at least one or more of the following: [2-[N-bis-(3-dimethylaminopropyl)-amino]-4-[2,3-dihydro-3-methyl-(benzo-1,3-thiazol-2-yl)-methylidene]-1-phenyl-quinolinium]$^+$; 4', 6-diamidino-2-phenylindole; bisbenzimide dyes; Cyanine Dyes including TOTO and YOYO family of dyes, ethidium bromide, and Sybr Green; anthraquinone dye, in particular DRAQ5; and/or functional derivatives or analogues thereof.

3. The method of claim 1, characterized in that the sample is a total RNA preparation sample or a polyA$^+$ sample.

4. The method of claim 1, characterized in that from ing to 2000 ng RNA, preferably from 10 ng to 1000 ng RNA template is used.

5. The method of claim 1, characterized in that said reverse transcriptase (RT) is selected from the group of Omniscript-RT, Sensiscript-RT, AMV-RT, M-MLV-RT, HIV-RT, EIAV-RT, RAV2-RT, SuperScript-RT, and/or derivatives thereof.

6. The method of claim 1, characterized in that its reactions take place in one reaction vessel.

7. The method of claim 1, characterized in that the fluorescence is measured at various time points during the reverse transcriptase reaction.

8. The method of claim 1, further comprising determining efficiency and/or reaction kinetics of a reverse transcriptase reaction.

9. The method of claim 8, wherein the efficiency of a reverse transcriptase is measured.

* * * * *